United States Patent
Perrier et al.

[11] Patent Number: 5,869,069
[45] Date of Patent: Feb. 9, 1999

[54] LIPOPHILIC HYDROXYLATED ACID, ITS USE IN COSMETICS AND PHARMACY, AND ITS PROCESS OF PREPARATION

[75] Inventors: Eric Perrier, Vienne; Daniele Antoni, Vernaison; Alain Huc, Sainte FDY les Lyon, all of France

[73] Assignee: Coletica, Lyons, France

[21] Appl. No.: 557,154

[22] PCT Filed: Jul. 21, 1995

[86] PCT No.: PCT/FR95/00984

§ 371 Date: Feb. 16, 1996

§ 102(e) Date: Feb. 16, 1996

[87] PCT Pub. No.: WO96/03110

PCT Pub. Date: Feb. 8, 1996

Related U.S. Application Data

[63] Continuation-in-part of Ser. No. 354,228, Dec. 12, 1994, abandoned.

[30] Foreign Application Priority Data

Jul. 22, 1994 [FR] France .................................. 94 09091

[51] Int. Cl.⁶ ..................................................... A61K 7/00
[52] U.S. Cl. .......................... 424/401; 514/506; 514/529; 514/553; 514/844; 514/846
[58] Field of Search ............................. 424/401; 514/558, 514/553, 844, 846, 506, 529

[56] References Cited

U.S. PATENT DOCUMENTS

| | | | |
|---|---|---|---|
| 4,070,150 | 1/1978 | Katz ......................................... | 432/210 |
| 4,078,147 | 3/1978 | Ukai et al. . | |
| 4,133,857 | 1/1979 | Takano ..................................... | 264/120 |
| 4,197,316 | 4/1980 | Yu ............................................ | 424/317 |
| 4,846,991 | 7/1989 | Suzue ..................................... | 252/89.1 |
| 4,959,206 | 9/1990 | Noguera ..................................... | 424/70 |
| 5,091,171 | 2/1992 | Yu et al. . | |
| 5,244,665 | 9/1993 | Natraj et al. . | |
| 5,302,377 | 4/1994 | Pereira et al. . | |
| B1 5,091,171 | 9/1995 | Yu et al. . | |

FOREIGN PATENT DOCUMENTS

| | | |
|---|---|---|
| A-0 261 812 A1 | 3/1988 | European Pat. Off. . |
| A-0 282 289 A1 | 9/1988 | European Pat. Off. . |
| A-0 338 565 A1 | 10/1989 | European Pat. Off. . |
| A-0 447 064 A3 | 9/1991 | European Pat. Off. . |
| A-0 514 067 A1 | 11/1992 | European Pat. Off. . |
| A-0 526 302 A2 | 3/1993 | European Pat. Off. . |
| A-0 521 647 A3 | 7/1993 | European Pat. Off. . |
| A-0 599 819 A2 | 6/1994 | European Pat. Off. . |
| A-2 390 160 | 5/1978 | France . |
| A-15 43 929 | 1/1970 | Germany . |
| 78 14296 | 12/1978 | Germany . |
| 40 33 565 A1 | 4/1992 | Germany . |
| A-443 565 | 2/1968 | Switzerland . |
| A-449 852 | 4/1968 | Switzerland . |
| A-95-03032 | 2/1995 | WIPO . |

*Primary Examiner*—Gollamudi S. Kishore
*Attorney, Agent, or Firm*—Armstrong, Westerman, Hattori, McLeland & Naughton

[57] ABSTRACT

The invention relates to new lipophilic hydroxylated acids wherein said lipophilic hydroxylated acid comprises a hydrophobic hydrocarbon chain having from 7 to 30 carbon atoms grafted onto the hydroxyl functional group and/or the acid functional group of the lipophilic hydroxylated acid via a covalent bond chosen from the group consisting of an ester bond on the hydroxyl functional group, an anhydride bond on the acid functional group and an amide bond on the acid functional group, provided that, in the case of an amide bond, this hydrophobic hydrocarbon chain consists of an alkyl radical having from 10 to 30 carbon atoms resulting from a monoamine, or a combination of these bonds. These new derivatives are useful as active ingredient of cosmetic or pharmaceutical compositions and as emulsifying agents.

7 Claims, 2 Drawing Sheets

LIPOPHILIC HYDROXYLATED ACID, ITS USE IN COSMETICS AND PHARMACY, AND ITS PROCESS OF PREPARATION

This application is a National Stage Application of PCT Application PCT/FR95/00984 and also a Continuation-in-Part Application of the pending U.S. Ser. No. 08/354,228, filed on Dec. 12, 1994 now abandoned.

BACKGROUND OF THE INVENTION

1. Field of the Invention

The present invention relates essentially to a new lipophilic hydroxylated acid, to its use in cosmetics and in pharmacy, and to its process of preparation.

SUMMARY OF THE PRIOR ART

It is known, from the article by Van Scott et al. in Arch. Dermatol., Vol. 110, October 1974, pages 586–590, to use α-hydroxylated acids in topical preparations in order to carry out a particularly effective keratolysis in the treatment of ichthyosis and of dry skins.

Likewise, Middleton has described, in J. Soc. Cosmet. Chem., 25 (1974), pages 519–534, a skin cream containing lactic acid or sodium lactate in order to reduce the dry skin forming scales in the corneal layer or stratum corneum.

The use of α-hydroxylated acid derivatives, by topical use, for treating a dry skin associated with eczema has also been published by Malcolm W. Greaves in Cosmetics and Toiletries, Vol. 105, October 1990, pages 61–64. This article emphasises, on page 61, right-hand column, second last paragraph, that, like urea, α-hydroxylated acids have been restricted in use due to their irritant nature. This article relates to the use of a composition containing a methoxypropylgluconamide with a lower acidity. This compound is also the subject of European Patent Application EP-A-0,338,565 of Revlon.

This European application relates to a compound of formula:

in which formula p is an integer from 1 to 4, $(C_nH_{2n})$ is a straight- or branched-chain alkyl bridge in which n is an integer from 1 to 6, and $(C_mH_{2m-1})$ is a straight- or branched-chain alkyl group in which m is an integer from 1 to 6.

These compounds are therefore amide derivatives of an at least dihydroxylated acid necessarily containing an ether chain, which compounds are different from those developed and used in the context of the present invention.

Greaves et al. have observed that the compounds described in this document EP-A-0,338,565 have little effectiveness as keratolytic agents, hence the necessity to use them at very high concentrations. In addition, this keratolytic property cannot be modified as it is very similar from one product to another.

In contrast, in the context of the present invention, new compounds were able to be discovered whose activity can be modified from a very powerful activity to a much gentler activity.

The document EP-A-0,273,202, Van Scott et al., describes additives based on hydroxycarboxylic acid which promote the topical actions of therapeutic agents present in an amount ranging from 0.01 to 99 weight % of the total composition.

The α-hydroxylated acids, their salts and their lactone form described in the document EP-A-0,273,202 have a very strong keratolytic power when they are used at high concentrations and at acid pH values. However, under such conditions of use, they are poorly tolerated by the skin surface and cause stinging, red blotches and inflammatory phenomena, which greatly restricts their use under such conditions.

In the present invention, new products have been discovered which are non-irritant in a wide pH range which can range from a very acidic pH in the region of 3 or 3.5 to a neutral pH of the order of 7, even when they are tested at very high concentrations such as 100%.

Hydroxylated acid amides obtained with a monoamine or a diamine which can in particular contain a $C_1$–$C_8$ alkyl radical are also known from the documents Van Scott U.S. Pat. No. 4,105,783 and 4,197,316. In the context of the invention, when it concerns amides, the latter are obtained with a monoamine having a $C_{10}$–$C_{30}$ fatty alkyl radical.

The document Revlon EP-A-0,447,064 also relates to alkoxyamides of the type of those described in the above document EP-A-0,338,565 which are different from those developed and used in the context of the present invention.

Various other documents relate to esters of the hydroxylated acid acid functional group which are different from those developed and used in the context of the present invention. These documents relating to esters are WO-A-95/03032, EP-A-0,599,819 Van Scott, EP-A-0,273,202; EP-A-0,521,647 Unilever in which citric acid fatty acid esters are described in which the acid functional groups of the citric acid are necessarily substituted by ester bonds with an ester substitution group $R_1$, $R_2$ and $R_3$. The hydroxyl functional group of the citric acid can be substituted by an acyl group $R_4$ which is preferably an acyl group having from 2 to 4 carbon atoms. In the context of the invention, ester bonds on the acid group of the hydroxylated acid are not sought for and an ester bond from the hydroxyl functional group of the hydroxylated acid comprises at least 7 carbon atoms.

The application from l'Oréal EP-A-0,526,302 relates to 2,5-dihydroxybenzenecarboxylic acid salts or esters in which the esters are produced on the acid functional group which are different from those developed and used in the context of the present invention. Mention may be made, as other esters of the acid functional group of the hydroxylated acid, of the documents Unilever EP-A-0,282,289; EP-A-0,261,812; the document U.S. Pat. No. 5,302,377 of Croda; the document U.S. Pat. No. 4,078,147 Ukai; Swiss Patents CH-A-449,852 and 443,565 of the Laboratoires Prod'Hyg, French Patent Henkel FR-A-2,390,160; and the document Henkel DE-4,033,565.

Mention will further be made, as amide, of German document DE-A-1,543,929 which describes amides of 2,4-dihydroxy-3,3-dimethylbutyric acid from a $C_5$ to $C_{30}$ hydroxyalkylamine or alkoxyalkylamine, i.e. a different amine from the alkylamines of the invention having $C_{10}$–$C_{30}$.

Moreover, topical compositions intended for skin treatment based on salicylic acid derivatives are also known from the document FR-A-2,581,542 of l'Oréal. These derivatives correspond to the formula:

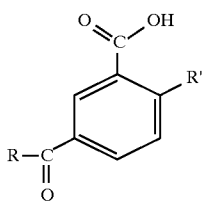

in which R represents a hydrocarbon chain which can have up to 17 carbon atoms and R' can represent a hydroxyl functional group or an ester functional group of the formula

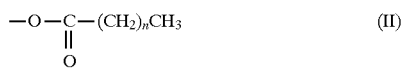

containing from 2 to 16 carbon atoms, it being possible for this chain to be saturated or unsaturated and for n to have a value between 0 and 14 (see the description and claim 1 in particular).

The preferred compounds are those in which R' denotes a hydroxyl functional group and R an alkyl group having from 3 to 11 carbon atoms (claim 2 and page 3, lines 10 to 20).

It emerges from this formula that these derivatives are necessarily substituted in position 5 of the phenyl ring by a radical containing a ketone functional group which appears to be the determining factor in providing a keratolytic activity greater than that of salicylic acid, as indicated in the description on page 2, lines 5 to 10.

In the context of the present invention, new hydroxylated acid derivatives have been discovered which are particularly active and non-irritant, including salicylic acid derivatives other than derivatives substituted in position 5 of the phenyl ring of the salicylic acid which are described in this document.

In addition, it has been discovered that the derivatives of the invention also exhibited a significant emulsifying power which makes it possible to use them as the sole emulsifying agent, that is to say used alone, or as a coemulsifying agent, making it possible to reduce the amount of other emulsifying agents.

Moreover, the 5-keto-substituted derivatives of salicylic acid described in the above document FR-A-2,581, 542 have the major disadvantage that the ketone bond cannot be hydrolyzed enzymatically. In addition, although an ester functional group is provided on the hydroxyl functional group, the only derivative prepared is the acetyl ester in Preparation Example G which appears, from the pharmacology tests of Tables I and II, to be less active than the free derivatives.

In fact, this document FR-A-2,581,542 teaches those skilled in the art the necessity of using derivatives substituted in position 5 of the salicylic acid by a ketone bond and the fact that the hydroxyl functional group of the salicyclic acid must be free.

This is confirmed by the document FR-A-2,607,498 of l'Oréal which relates to lipophilic quaternary ammonium salicylates in which the hydroxyl functional group of the salicylic acid is unsubstituted and which always contains, in position 5, the radical bonded by a ketone bond to the phenyl ring, this salicylate being in the ionic form by virtue of the presence of a quaternary ammonium which comes to be coupled to the COO⁻ functional group of the acid. Consequently, these documents dissuade those skilled in the art from searching for salicylic acid derivatives other than the 5-keto-substituted derivatives, that is to say carrying a radical bonded by a ketone bond.

These compounds, however, have the disadvantage that they are not hydrolyzable, either spontaneously or under the action of skin or bacterial enzymes.

Document EP-A-0,378,936 also uses the same salicylic acid derivatives to carry out skin ageing treatment, which derivatives have the same disadvantages of not being hydrolyzable, either spontaneously or under the action of skin or bacterial enzymes.

Moreover, the document EP-A-0,433,104 of Unilever relates to a shampoo composition containing 2-hydroxyalkanoic acid in combination with a buffering agent forming a coacid, so that the pH of the composition is preferably between 3 and 5.

Further, the document EP-A-0,413,528 of Yu and Van Scott relates to amphoteric compositions and to polymer forms of α-hydroxy acid and to their therapeutic use in treating dry skins, acne, keratosis, psoriasis, eczema, ageing blotches, wrinkles, pallid skin, hyper-pigmented skin, hyper-keratinized skin, inflammatory dermatoses or skin changes associated with age and as skin-cleaning product. In fact, as emerges from the list given on pages 29 and 30, it concerns the same hydroxy acids as those which are described in the document EP-A-0,273,202 analyzed above. These products are poorly tolerated by the skin surface and cause stinging, red blotches and inflammatory phenomena which greatly restrict their use.

A similar document further consists of the document EP-A-0,508,324 filed by Yu and Van Scott for treating signs of ageing of the skin, of the nails and of the hair.

Finally, the document EP-A-0,585,170 is also a l'Oréal document relating to a composition for treating acne containing the quaternary ammonium salt of the 5-ketone derivative of salicylic acid with a quaternary ammonium ion, encapsulated in liposome-type vesicles.

It is thus observed that the prior art demonstrates that intensive research is being carried out regarding the use of α-hydroxylated acids in cosmetic or pharmaceutical compositions but that none of the solutions proposed has been capable of simultaneously solving the problem of tolerance of these products by the skin surface, the acids being too harmful, and the problem of their modifiable effectiveness, as well as of their biocompatibility in being degradable or hydrolyzable spontaneously or under the action of skin or bacterial enzymes. In addition, their affinity with respect to lipid constituents of the epidermis remains limited.

SUMMARY OF THE INVENTION

The aim of the present invention is to solve the new technical problem consisting in providing new products which can be used as cosmetic or pharmaceutical and/or dermatological products having a greater affinity with respect to lipid constituents of the epidermis, in particular the stratum corneum, which are non-irritant and which have a modifiable effectiveness.

Another main aim of the present invention is to solve the new technical problem consisting in providing new products which can be used as cosmetic or pharmaceutical and/or dermatological products having excellent biocompatibility, especially in being hydrolyzable either spontaneously or under the action of skin or bacterial enzymes.

Another aim of the present invention is to solve these new technical problems according to a solution which makes it possible to provide compounds having good keratolytic activity in being capable of reaching the desmosomes and the nascent layers of the stratum corneum.

A further aim of the present invention is to solve the new technical problem consisting in providing a solution which makes it possible to provide products having anti-acne and/or anti-wart and/or anti-eczema and/or -anti-psoriasis and/or anti-dandruff and/or anti-dry skin and/or anti-wrinkle and/or anti-age activity, without significant irritant power.

A further aim of the present invention is to solve the new technical problem consisting in providing a solution which makes it possible to produce new agents which improve skin moisturizing, elasticity and cohesion as well as new depigmenting agents, without significant irritant power.

Another main aim of the present invention is to solve the new technical problem consisting in providing a solution which makes it possible to produce new products which have an excellent emulsifying ability which makes it possible to use them either as the sole emulsifying agent or as a coemulsifying agent, thus making it possible to reduce the concentration of other emulsifying agents used, in particular during the manufacture of cosmetic or pharmaceutical and/or dermatological compositions.

It has been found entirely unexpectedly that all these technical problems could be solved by providing new hydroxylated acid derivatives, described below. It has also been discovered that the effectiveness of these new derivatives was increased when these derivatives are used when present in the final reaction mixture with the unreacted starting acids.

Thus, according to a first aspect, the present invention provides new lipophilic hydroxylated acids, said hydroxylated acids comprising at least one hydroxyl functional group and at least one acid functional group, wherein said lipophilic hydroxylated acid comprises a hydrophobic hydrocarbon chain having from 7 to 30 carbon atoms grafted onto the hydroxyl functional group and/or the acid functional group of the hydroxylated acid via a covalent bond chosen from the group consisting of an ester bond on the hydroxyl functional group, an anhydride bond on the acid functional group, an amide bond on the acid functional group, provided that, in the case of an amide bond, this hydrophobic hydrocarbon chain consists of an alkyl radical having from 10 to 30 carbon atoms resulting from a monoamine, or a combination of these bonds.

According to a first embodiment, this lipophilic hydroxylated acid is one wherein the hydroxylated acid, before grafting of the abovementioned hydrophobic hydrocarbon chain, comprises a saturated or unsaturated, straight or branched or cyclic chain having from 2 to 30 carbon atoms.

According to another embodiment, this lipophilic hydroxylated acid is one wherein the grafting of the abovementioned hydrophobic hydrocarbon chain is carried out by reaction of a hydroxylated acid with a monoamine containing an alkyl radical containing a straight, branched or cyclic chain having from 10 to 30 carbon atoms or, in the case of the formation of ester bonds on the hydroxyl functional group of the hydroxylated acid or of an anhydride bond on the acid functional group of the hydroxylated acid, with an acid comprising from 7 to 30 carbon atoms, it being possible for said hydrophobic hydrocarbon chain of the acid to be saturated or unsaturated, linear or branched or cyclic, without another functional group on its skeleton or with other functional groups, in particular acid, alcohol and/or amine functional group(s).

According to yet another embodiment, this lipophilic hydroxylated acid is one wherein said hydroxylated acid is mono- or polyhydroxylated and is a monoacid or a polyacid.

According to another embodiment, this lipophilic hydroxylated acid is one which has the hydroxylated acid, before grafting of the hydrophobic hydrocarbon chain, comprises from 2 to 18 carbon atoms.

According to another embodiment, this lipophilic hydroxylated acid is one wherein the hydroxylated acid, before grafting of the abovementioned hydrophobic hydrocarbon chain, is chosen from the group consisting of an α-hydroxylated acid, such as glycolic acid, lactic acid, malic acid, tartaric acid, gluconic acid, citric acid, methyllactic acid, mandelic acid, atrolactic acid, phenyllactic acid, glyceric acid, benzilic acid, α-hydroxybutanoic acid, α-hydroxyhexanoic acid, α-hydroxyheptanoic acid or α-hydroxyoctanoic acid; a β-hydroxylated acid, such as salicylic acid or serine; and a polymer or a copolymer of this hydroxylated acid, or their mixtures.

Naturally, as is very easily understood by those skilled in the art, this list is not in any way exhaustive since all hydroxylated acids can be used in the context of the invention. It is a further advantage of the invention that acids having a hydroxyl functional group a long way from the acid functional group can advantageously be used. The invention thus covers the use of any hydroxylated acid without limitation. However, the hydroxylated acids currently preferred are the acids which have a starting hydrocarbon chain of 2 to 30 carbon atoms and more preferably of 2 to 18 carbon atoms.

According to another embodiment, this lipopholic hydroxylated acid is one which has a ratio by weight of the hydroxylated acid to the hydrophobic chain of 0.05 to 10, and preferably of 0.05 to 2.

According to a second aspect, the present invention also relates to the use of the lipophilic hydroxylated acid as active ingredient of a cosmetic composition or of a dermatological and/or pharmaceutical composition and/or as emulsifying agent.

According to a specific embodiment, the use is one wherein the abovementioned lipophilic hydroxylated acids, as active principle, exhibit a keratolytic activity, a chemical exfoliation activity deep in the skin, which makes it possible to improve the subsequent penetration by other active ingredients, a stimulating activity of the cell functions, which improves the elasticity and the cohesion of the skin, a depigmenting activity, an anti-wrinkle or anti-age activity, a moisturizing activity which makes it possible to treat dry and ichthyotic skins, or an anti-acne, anti-wart, anti-eczema, anti-psoriasis or anti-dandruff activity.

According to yet another specific embodiment, the use is one wherein the abovementioned lipophilic hydroxylated acids constitute particularly advantageous emulsifying agents, where they are used as sole emulsifying agent or as a coemulsifying agent. Moreover, when they are used as active principle at relatively high concentrations, it is not necessary, due to their emulsifying activity, to use other emulsifying agents, which constitutes an unexpected technical effect which is particularly advantageous in the formulation of the cosmetic, pharmaceutical and/or dermatological composition in so far as the usual emulsifying agents always present risks of bioincompatibility.

According to a third aspect, the present invention also covers a composition chosen from the group consisting of a cosmetic, pharmaceutical and/or dermatological composition, wherein it comprises, as active ingredient and/or as emulsifying agent, at least one lipophilic hydroxylated acid mentioned above.

According to a specific embodiment, the composition is one wherein the proportion of lipophilic hydroxylated acid is between 0.001 weight % and 50 weight % of the final composition, preferably between 1 weight % and 20 weight % of the final composition.

According to another specific embodiment, the composition is one wherein the abovementioned lipophilic hydroxylated acid is the reaction product of a hydroxylated acid chosen from the group consisting of malic acid, glycolic acid, gluconic acid, salicylic acid, lactic acid, serine, a glycolic acid polymer, a lactic acid polymer or a glycolic acid and lactic acid copolymer and of a compound comprising the abovementioned hydrophobic hydrocarbon chain chosen from the group consisting of a halide or anhydride of stearic acid, palmitic acid, myristic acid, lauric acid, octanoic acid, decanoic acid, undecylenic acid, undecanoic acid, oleic acid, linolenic acid, linoleic acid or acetic acid or of their succinic or maleic derivatives.

According to another embodiment, the composition is one wherein the abovementioned lipophilic hydroxylated acid is the reaction product of a hydroxylated acid with a monoamine containing an alkyl radical containing a straight, branched or cyclic chain having from 10 to 30 carbon atoms.

According to a fourth aspect, the present invention further covers a process for the manufacture of the abovementioned lipophilic hydroxylated acid, wherein it comprises the reaction of a hydroxylated acid with a halide or an anhydride of an acid comprising a hydrophobic hydrocarbon chain having from 2 to 30 carbon atoms or with a monoamine containing an alkyl radical containing a straight, branched or cyclic chain having from 10 to 30 carbon atoms.

According to a specific embodiment, the process is one wherein the abovementioned hydroxylated acid, or acid halide or anhydride, or monoamine are as defined above.

According to another specific embodiment, the manufacturing process is one wherein, for the grafting of a hydrophobic hydrocarbon chain originating from an acid, a halide or an anhydride of the acid is used as starting material.

According to another specific embodiment, the process is one wherein, for the grafting of a hydrophobic hydrocarbon chain originating from a monoamine, use is made as starting material of a monoamine which is reacted with the hydroxylated acid in the presence of a catalyst, of a bifunctional agent or of an enzyme.

This bifunctional agent is well known to those skilled in the art. Particularly preferred bifunctional agents are a carbodiimide, in particular N-(3-dimethylaminopropyl)-N'-ethylcarbodiimide hydrochloride, oxalyl chloride, diphenylphosphoryl azide, propanephosponic anhydride or any other agent commonly used as coupling agent during linear peptide syntheses.

According to yet another specific embodiment, the process is one wherein an enzymatic grafting of a hydrophobic hydrocarbon chain onto the hydroxylated acid is carried out. Such enzymes capable of carrying out this grafting are well known to those skilled in the art. For example, mention could be made of an industrial lipase, for example the enzyme commercially available under the trade name Lipozyme®, manufactured by the company Novo®. This enzymatic grafting is particularly advantageous for grafting amines.

According to another specific embodiment, the process is one wherein the reaction takes place at a temperature between approximately 0° C. and approximately 100° C., preferably at room temperature, in aqueous medium or an organic solvent.

It should be noted that the grafting reactions can be carried out at high temperature (between 80° and 100° C.) to give higher yields but involve more stresses and risks of deterioration of the products.

Moreover, the relative proportions of the hydroxylated acid to the substance introducing the hydrophobic hydrocarbon chain can vary within wide limits. Thus, the relative proportions by weight, used during the reaction, can vary from 5/95 to 95/5, preferably from 5/95 to 50/50.

Moreover, it can be advantageous first of all to neutralize the hydroxylated acid to a pH in the region of neutrality, that is to say in the region of 7. It is also possible to provide for maintaining the pH of the reaction at a basic value during the reaction.

In this case, it is possible to adjust the pH continuously either using a strong base of the NaOH or KOH type or to provide a buffer such as phosphate, carbonate, borate or citrate or the addition of a molecule suitable for continuously trapping the acid manufactured during the reaction, such as triethanolamine (TEA), cyclohexylamine, and the like.

Moreover, after the reaction, it can also be advantageous to adjust the pH according to the applications envisaged, generally between approximately 2 and approximately 7. It can also be advantageous to lyophilize the final reaction mixture in order to obtain a lyophilized product containing all the products of the reaction mixture, namely the lipophilic hydroxylated acid mixed with the unreacted starting material(s), in particular the acids and/or monoamines, which is particularly advantageous in the context of the invention.

Sterilization can optionally be carried out conventionally, especially in the context of a cosmetic, pharmaceutical or dermatological use, for example by β- or γ-rays.

By virtue of the invention, new lipophilic hydroxylated acids are obtained which possess a greater affinity with respect to the lipophilic constituents of the stratum corneum and are thus capable of becoming integrated more easily throughout the thickness of the stratum corneum.

In addition, by virtue of the grafting of a lipophilic group onto the hydroxylated acids, via ester bonds on the hydroxyl functional group and/or amide and anhydride bonds on the acid functional group of the hydroxylated acid, bonds are used which are hydrolyzable by enzymatic systems naturally present in the skin, such as lipases and proteases, and at the surface of the latter, such as enzymes released by saprophytic microorganisms present in very large numbers on the skin.

Thus, the new compounds of the invention make it possible, by a natural hydrolysis, progressively to release the hydroxylated acids, which makes it possible to obtain the use of their activity at the site where the hydroxylated acid will have been conveyed or transported by the lipophilic grafting and to obtain a delayed effect while maintaining this activity over long periods of time, which makes it possible unexpectedly to reduce the concentrations of use.

It could also be observed that the products according to the invention are essentially non-irritant, in contrast to the hydroxylated acids previously used.

The products of the invention also exhibit new activities which have been stated above.

In particular, these products are particularly effective emulsifying agents. Thus, the invention also covers a composition comprising, as emulsifying agent, at least one lipophilic hydroxylated acid, in particular at a concentration of between 0.1 weight % and 50 weight % of the final composition, preferably between 1 weight % and 20 weight % of the final composition.

In the context of the invention, it is preferred that the products are not purified, that is to say that they are present in the reaction mixture comprising the unreacted starting acids, which means that only a part (from 5 to 90 mol %, and most often 10 to 30 mol %) of the hydroxylated acids are converted to esters, to amides or to anhydrides, the other part being complexed more or less intensively to the hydrophobic chains via ionic bonds, bonds of Van der Waals type, hydrophilic bonds and hydrophobic bonds. In the case where the process of preparation involves the use of a non-aqueous solvent, this non-aqueous solvent generally being incompatible with a cosmetic, pharmaceutical and/or dermatological use, this solvent will usually be removed.

They then take part, in the pure state or, preferably, in the crude manufacturing state, that is to say in the final reaction mixture comprising the unreacted starting acids, in the formulations of cosmetic, pharmaceutical and/or dermatological preparations.

The lipophilic hydroxylated acids according to the invention can advantageously be presented in a dry form, in particular a lyophilized form.

In the context of the present description and claims, the terms "monoamine containing an alkyl radical having from 10 to 30 carbon atoms" relate to an amine comprising a single amine functional group which is monosubstituted or disubstituted by an alkyl radical having from 10 to 30 carbon atoms, that is to say having a linear, branched or cyclic fatty chain. Such monoamines containing a fatty chain are well known to the person skilled in the art and laurylamine or stearylamine will be mentioned by way of example.

According to a fifth aspect, the present invention also relates to a method for keratolytic treatment, for cosmetic or therapeutic use, on regions of the skin having need thereof, comprising the application to said regions of the skin of a keratolytic effective amount of at least one lipophilic hydroxylated acid compound which is the reaction product of a hydroxylated acid having at least one acid functional group and at least one hydroxyl functional group with a hydrophobic hydrocarbon component having a hydrophobic hydrocarbon chain having from 7 to 30 carbon atoms, grafted onto one or both of said hydroxyl and acid functional groups via a covalent bond chosen from the group consisting of an ester bond on the hydroxyl functional group, an anhydride bond on the acid functional group and an amide functional group on the acid functional group, provided that, in the case of an amide bond, this hydrophobic hydrocarbon chain consists of an alkyl radical having from 10 to 30 carbon atoms resulting from a monoamine, or a combination of these bonds.

Preferred embodiments of the method are clearly apparent to a person skilled in the art from the description taken in its entirety and including all the claims which are incorporated by reference.

According to a sixth aspect, the invention also relates to a treatment method, for cosmetic or therapeutic use, for chemical exfoliation of the skin, for stimulating the cells of the skin, for improving the elasticity and the cohesion of the skin, for depigmenting the skin, for moisturizing the skin, or for producing an anti-wrinkle effect on the skin, an anti-aging effect on the skin, an anti-acne effect on the skin, an anti-wart effect, an anti-eczema effect, an anti-psoriasis effect on the skin and an anti-dandruff effect on the regions of the hair and of the scalp, comprising the application to said skin, to the hair or to the scalp having need thereof of an effective amount of a lipophilic hydroxylated acid compound which is the reaction product of a hydroxylated acid having at least one acid functional group and at least one hydroxyl functional group with a hydrophobic hydrocarbon component having a hydrophobic hydrocarbon chain having from 7 to 30 carbon atoms grafted onto one or both of said hydroxyl and acid functional groups via a covalent bond chosen from the group consisting of an ester bond on the hydroxyl functional group, an anhydride bond on the acid functional group and an amide functional group on the acid functional group, provided that, in the case of an amide bond, this hydrophobic hydrocarbon chain consists of an alkyl radical having from 10 to 30 carbon atoms resulting from a monoamine, or a combination of these bonds. Similarly, preferred embodiments of the method are clearly apparent to the person skilled in the art from the description taken in its entirety and including all the claims which are incorporated for reference.

Other aims, characteristics and advantages of the invention will become clearly apparent in the light of the explanatory description which will follow, made with reference to the examples below, given simply by way of illustration and which could in no way limit the scope of the invention. However, it is to be observed that these examples clearly contain, for those skilled in the art, general information and consequently make it possible to support claims of general scope. In all the examples, the percentages are given by weight, except when otherwise indicated.

DESCRIPTION OF THE EXAMPLES

Example 1 of the Invention

Figure 1:
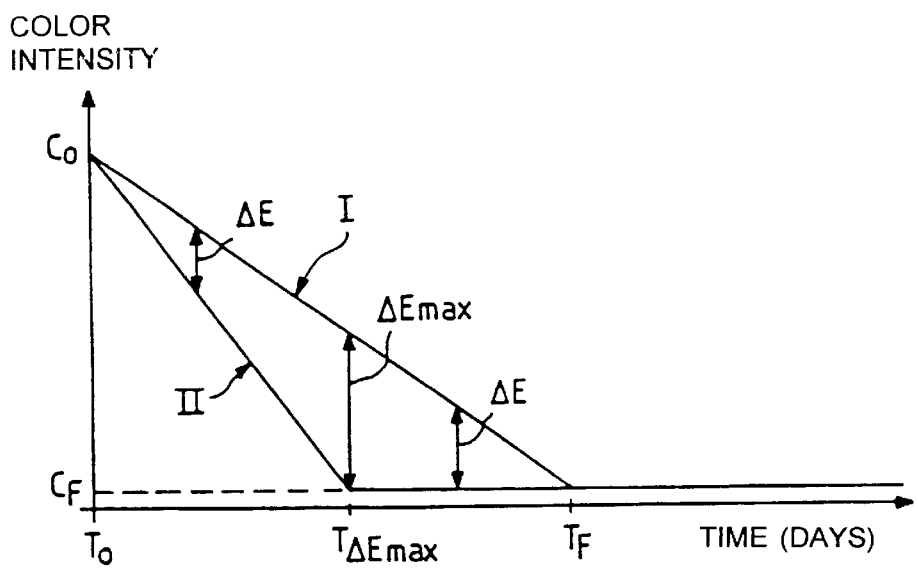
FIG. 1 shows standard curves which can be obtained when keratolytic tests are carried out. These curves are obtained by plotting the time, in days, on the abscissa and the color intensity, as measured by a chromameter, in this case a Minolta®, on the ordinates. The color intensity on day $T_0$, reference $C_0$, is obtained by applying an emulsion containing dihydroxyacetone (DHA) as coloring agent as described in Example 20. Curve I is obtained by measuring the color intensity with the chromameter as a function of the time expressed in days, without any specific intervention. Curve II is obtained by applying one of the keratolytic formulations tested, expressed in the same way. The difference between the two curves, expressed as $\Delta E$, measures the keratolytic strength of the keratolytic formulation as a function of time. The sum of the $\Delta E$ values, which represents the area or surface defined between Curves I and II, represents the overall keratolytic performance of the keratolytic formulation tested and is the subject of FIG. 3.

Lipophilic Hydroxylated Acid comprising a Stearic Acid and Malic Acid Ester and Anhydride Mixture 100 g of malic acid are placed in 500 ml of demineralized water. The reaction mixture is adjusted to a pH of 11 with a sodium hydroxide solution (NaOH, 12N). 100 g of stearic acid chloride are slowly added with very vigorous stirring of Ultraturrax or Silverson type (10,000 to 20,000 rpm).

The pH moves in a few tens of minutes from a value of 11 to a value close to 1, when no buffer is added to the reaction mixture.

After a reaction time of approximately 1 h, the whole mixture is neutralized to a pH of between 2.0 and 7.0 with a sodium hydroxide solution (NaOH, 12N).

The whole mixture can then preferably be lyophilized and then optionally sterilized by γ- or β-rays.

The product exists in the form of a very white pulverulent powder which can be placed both in the aqueous phases and in the oily phases of cosmetic preparations.

Part of the hydroxylated acid (malic acid) exists in the form of a fatty acid ester and anhydride and part, which has not reacted, is in a form tightly complexed via hydrogen bonds and via Van der Waals bonds.

This product therefore comprises stearic acid and malic acid esters and anhydrides, the anhydride functional group being between the acid functional group of the malic acid and the acid functional group of the stearic acid and the ester functional group being obtained between the acid functional group of the stearic acid and the hydroxyl functional group of the malic acid. This grafting takes place both on the acid functional group and on the hydroxyl functional group. Moreover, the product obtained also comprises the unreacted starting acids, optionally in the salt form, depending on the final pH after neutralization and on the $pK_a$ of the acids used.

It has been discovered according to the present invention that the final reaction mixture can be used as is, without specific purification or separation, to constitute a cosmetic or pharmaceutical or dermatological active principle and/or as emulsifying agent, which constitutes a determining advantage of the present invention.

Harmlessness tests, based on an absence of skin and eye irritation, were carried out with this product and form the subject of Example 17.

Example 2 of the Invention

Lipophilic Hydroxylated Acid comprising a Palmitic Acid and Glycolic Acid Ester and Anhydride Mixture The same grafting process is used as that described in Example 1 but glycolic acid is used in place of malic acid and palmitic acid chloride in place of stearic acid chloride.

A palmitic acid and glycolic acid ester and anhydride mixture is thus obtained, as well as the unreacted starting acids. The final crude reaction mixture can be used as is.

Example 3 of the invention

Lipophilic Hydroxylated Acid comprising a Lauric Acid and Gluconic Acid Ester and Anhydride Mixture The same process is used as that described in Example 1, except that gluconic acid is used in place of malic acid and lauric acid chloride is used in place of stearic acid chloride.

The final reaction mixture can be used as is.

Example 4 of the Invention

Lipophilic Hydroxylated Acid comprising an Undecylenic Acid and Salicylic Acid Ester and Anhydride Mixture By carrying out the reaction according to the process described in Example 1, but using salicylic acid in place of malic acid and undecylenic acid chloride in place of stearic acid chloride, the title compound is obtained as a mixture with the unreacted starting acids.

The final reaction mixture can be used as is.

Example 5 of the Invention

Lipophilic Hydroxylated Acid comprising a Mixture of Esters and Anhydrides of Palmitic and Oleic Acid and of Polymers of Various Acids Example 5a Grafting a Palmitic and Oleic Acid Chloride Mixture (80/20 w/w) onto a Glycolic Acid Polymer The reaction is carried out as described in Example 1 but a glycolic acid polymer of molecular weight 10,000 to 700,000 D is used in place of malic acid and a palmitic and oleic acid chloride mixture (80/20 w/w) is used in place of stearic acid chloride.

The final reaction mixture can be used as is.

Example 5b

Reaction Product of a Lactic Acid Polymer with a Palmitic and Oleic Acid Chloride Mixture (80/20 w/w)

The reaction is carried out as described in Example 1, except that a lactic acid polymer, molecular weight 10,000 to 700,000 D, is used in place of malic acid and a palmitic and oleic acid chloride mixture (80/20 w/w) is used in place of stearic acid chloride.

The final reaction mixture can be used as is.

Example 5c

Reaction Product of a Lactic Acid and Glycolic Acid Copolymer with a Palmitic and Oleic Acid Chloride Mixture (80/20 w/w)

The reaction is carried out as described in Example 1, except that a lactic acid and glycolic acid copolymer of molecular weight 10,000 to 100,000 D is used and a palmitic and oleic acid chloride mixture (80/20 w/w) is used in place of stearic acid chloride.

The final reaction mixture can be used as is.

Example 6 of the Invention

Lipophilic Hydroxylated Acid comprising a Stearic and Linolenic Acid and Serine Ester and Anhydride Mixture The reaction is carried out as described in Example 1, except that serine is used in place of malic acid and a stearic and linolenic acid chloride mixture (80/20 w/w) is used in place of stearic acid chloride.

The final reaction mixture can be used as is.

Example 7 of the Invention

Lipophilic Hydroxylated Acid comprising an Acetic Acid and Tartaric Acid Ester and Anhydride Mixture The reaction is carried out as described in Example 1, except that tartaric acid is used in place of malic acid and acetic anhydride is used in place of stearic acid chloride.

The final reaction mixture can be used as is.

Example 8 of the Invention

Example 8a

Lipophilic Hydroxylated Acid comprising a Succinic Acid and Tartaric Acid Ester and Anhydride Mixture The reaction is carried out as described in Example 1 but tartaric acid is used in place of malic acid and succinic anhydride is used in place of stearic acid chloride.

The final reaction mixture can be used as is.

Example 8b

The reaction is carried out as described in Example 1, except that tartaric acid is used in place of malic acid and maleic anhydride is used in place of stearic acid chloride.

As for all the other examples, the final reaction mixture can be used as is.

Example 9 of the Invention

Lipophilic Hydroxylated Acid comprising a Stearic Acid and Lactic Acid Ester and Anhydride Mixture Whereas the reaction takes place in aqueous solvent in the preceding Examples 1 to 8, a reaction in organic solvent is described below.

1 mol of lactic acid is placed in a mixture composed of 1,000 ml of dichloromethane and 2 mol of triethanolamine (TEA).

1 mol of stearic acid chloride is then added dropwise to this mixture with stirring.

After reacting for a few minutes, the solvent is removed by distillation and the product recovered exists in the form of a white powder.

This product comprises, on the one hand, the sought-for lipophilic hydroxylated acid comprising anhydride and ester functional groups between the lactic acid and the stearic acid, and the unreacted starting acids.

This product formed by the final reaction mixture can be used as is.

Example 10 of the Invention

Lipophilic Hydroxylated Acid comprising the Anhydride and Ester Functional Groups of Lactic Acid and of Stearic Acid The reaction is carried out as described in Example 9, except that 2 mol of NaH, washed beforehand with hexane, are used in place of 2 mol of TEA. The reaction is carried out at a temperature close to 0° C.

This product formed by the final reaction mixture can be used as is.

Example 11 of the invention

Lipophilic hydroxylated acid comprising amide bonds by reaction of a hydroxylated acid with a monoamine containing a $C_{10}$–$C_{30}$ alkyl radical This example is general for the preparation of lipophilic hydroxylated acid comprising amide bonds.

In general, 1 mol of hydroxylated acid will be placed in a sufficient amount of water which is neutralized to a pH approximately equal to 7. A sufficient amount of phosphate buffer can be added to the mixture so as to obtain a 0.5M phosphate buffer. 1 mol of a carbodiimide is then added to the mixture with stirring.

The whole mixture can be stored with stirring for 1 h at room temperature or 24 h at 6° C. 1 mol of a monoamine containing a $C_{10}$–$C_{30}$ alkyl radical is then added to the mixture, with very powerful stirring of the Ultraturrax or Silverson type. After reacting for 4 h at room temperature, the whole mixture is adjusted to a pH of between 2 and 7, and preferably between 3 and 6, with 6N HCl.

A lyophilization, and optionally a sterilization with β- or γ-rays, can then be carried out.

The product obtained can be used as is as active principle of a cosmetic or pharmaceutical or dermatological composition.

It will be noted that the covalent bond which results from this reaction provides a hydroxylated amide, and other characteristic bonds are present between the amine and the hydroxylated acid, such as ionic bonds and bonds of Van der Waals type, which effectively participate in the activity of the product.

Example 12 of the Invention

Lipophilic Hydroxylated Acid comprising Amide Functional Groups by Reaction of Malic Acid with a Fatty Amine The reaction is carried out as described in Example 11, except that malic acid is used as hydroxylated acid, a fatty amine consisting of laurylamine or stearylamine is used as amine and a carbodiimide consisting of N-(3-dimethylaminopropyl)-N'-ethylcarbodiimide hydrochloride is used as bifunctional coupling agent.

The reaction mixture can be used as is or in a form which is lyophilized and optionally sterilized with β- or γ-rays. This can also be carried out in the context of all the other examples.

Example 13 of the Invention

Lipophilic Hydroxylated Acid comprising Amide Bonds

Example 13a

The reaction is carried out as described in Example 12 but a carbonate buffer at a 1M concentration is used as buffer. The carbodiimide and the amine are placed together in the reaction mixture and the pH is adjusted to 7 throughout the reaction.

The final reaction mixture can be used as is.

Example 13b

The reaction is carried out as described in Example 13a but a borate buffer at a 1M concentration is used.

The final reaction mixture can be used as is.

Example 13c

The reaction is carried out as described in Example 13a but a citrate buffer at a concentration of 0.5M is used.

The final reaction mixture can be used as is.

Example 14 of the Invention

Preparation of Lipophilic Hydroxylated Acid comprising Amide Bonds

The reaction is carried out as described in Example 12, except that oxalyl chloride (1 mol) is used as bifunctional agent in place of a carbodiimide.

The final reaction mixture can be used as is.

Example 15 of the Invention

Enzymatic Preparation of Lipophilic Hydroxylated Acid 100 g of laurylamine are placed to react with 50 g of malic acid and 25 g of an industrial lipase, for example Lipozyme® of NOVO®. The reaction is carried out in a closed reactor with stirring at 60° C. for 7 days. The grafting yield is 10% with respect to the starting laurylamine.

The product resulting from this grafting is used as is in the aqueous phase of a cosmetic formulation which can, for example, be produced at a pH of 3.

Example 16 of the Invention

Preparation of Lipophilic Hydroxylated Acid comprising Anhydride and Ester Bonds between Lactic Acid and Palmitic Acid The same grafting process is used as that described in Example 1 but lactic acid is used in place of malic acid and palmitic acid chloride is used in place of stearic acid chloride.

A palmitic acid and lactic acid ester and anhydride mixture is thus obtained, as well as the unreacted starting acids.

The reaction mixture is advantageously used as is.

It will be observed that in all the preceding examples, as for all the products of the invention, these products can be used as active principle of a cosmetic, pharmaceutical and/or dermatological composition or as emulsifying agent or simultaneously for both these purposes.

Tests demonstrating the activities of the products according to the invention are now described below.

Example 17 of the Invention

Harmlessness Tests by Absence of Skin and Eye Irritation

Harmlessness tests are carried out using the product which has been lyophilized and sterilized by γ-rays, in the form of a very white pulverulent powder, obtained in Example 1.

The skin and eye irritation studies are carried out according to protocols in agreement with EEC directives No. 404 (12, May 1980) and No. 405 (24 February 1987), in the following way:
 a) First of all, the pure product is used in the pulverulent form and at a pH of 7.
 b) The product obtained is used at a pH of 5.5 in the form of a 20 weight % solution in water, which represents 10 weight % of malic acid.
 c) The product is used at a pH of 3.5 in the form of a 20 weight % solution, which represents 10 weight % of malic acid.

The adjusting of this pH for each of these products is obtained by varying the final stage of Example 1. In fact, in Example 1, it is expected that, after a reaction time of approximately 1 h, the whole mixture is neutralized to a pH of between 2 and 7 with a sodium hydroxide solution. The pH of the final product can thus be adjusted.

The tests carried out according to the above protocols have made it possible to observe that the products seem to be non-irritant, were extremely well tolerated and caused no signs of cutaneous or eye irritation, whether they are at a pH of 7.5, 5 or even 3.5.

Moreover, oral administration of a maximum dose of 5 g of the product of the invention of Example 1 per kilogram of body weight caused no toxicity, this test being carried out in accordance with the EEC protocol relating to the study of oral toxicity of the EEC directive No. 401 of 24 Feb. 1987.

Example 18 of the Invention

In Vivo Allergy Test on Animals

Experimental Protocol

The test is carried out according to the experimental protocol described below, adapted from the method described by Magnusson and Kligman (J. Invest. Derm., 1969, 52, 268–276), which is recognized by the person skilled in the art as a reliable and reproducible method.

1. —Characterization of the experimental model
1.1—Animals used
 albino guinea pigs, Hartley strain, provided by the firm Maury (24610 Villefranche de Lonchat, France),
 weighing approximately 350 g at the beginning of the test,
 identified by individual branding with picric acid.
 Before the test, the animals are kept for 6 days under the same conditions as during the test.
1.2—Caging
 The animals are kept in 3 46.5 cm×31 cm×19 cm Makrolon boxes, the floors of which are covered with clean sawdust.
 A device for supplying food to the guinea pig and a feedbottle are attached to the lid which forms a grid made of stainless steel.
 The boxes are kept in a room:
  lit complementarily with natural and artificial light,
  with air conditioning: renewal of the air takes place 14 cycles per hour, the temperature is maintained at 22° C.±1° (upper and lower limit), and the relative humidity is maintained at 52% ±8 (upper and lower limit).
1,3—Food
 Animals receive tap water and food.
2—Test conditions
 2.1—Determination of the maximum non-irritatant concentration by topical application
 This test is carried out with 3 guinea pigs which received an injection of Freund's adjuvant 3 weeks previously. The different concentrations tested under semi-absorbent compress were 1/1, 1/2, 1/4 and 1/8. Dilutions were carried out with distilled water.
 2.2—Determination of the maximum irritating concentration by intradermal injection
 This control was not carried out due to the fact that the induction phase can be carried out with undiluted product.
 2.3—Final study
 It was carried out on 30 animals in groups of 15:
 GROUP 1 (control)
 GROUP 2 (treated).

INDUCTION PHASE

It was carried out as follows: Treated group: The following operations are carried out on all the animals in the scapular region on both sides of the vertebral axis:

A D0

Injection of 0.1 ml of 50% Freund's adjuvant in isotonic NaCl.

Injection of 0.1 ml of undiluted product.

Injection of 0.1 ml of a mixture of equal volumes of product and of Freund's adjuvant.

A D7

Application to the region of the injections of 1 ml of 10% sodium lauryl sulfate in petrolatum.

A D8

Application for 48 hours under semi-absorbent compress of 0.5 ml of the product as is.

Control group

The animals of this group receive the same treatment as those of the treated group but a saline solution is used in place of the product.

The animals of the two groups are then kept for 2 weeks.

CHALLENGE PHASE

On day D27, after they have been carefully restrained by restraining devices, the animals of the two groups receive, on a posterior region of the back, 0.5 ml of the test product consisting of the product of the invention obtained in Example 1, that is to say malic acid, at its maximum non-irritant concentration (MNIC) dose and at its MNIC half-dose, under semi-absorbent compress for 24 hours.

2.4—Macroscopic observations

Erythema and/or edema are recorded 24 and 48 hours after removing the pad or patch.

The scores are allocated according to the following grading scale:

|  |  |
| --- | --- |
| No reaction | 0 |
| Slight reaction | 1 |
| Moderate reaction | 2 |
| Major reaction | 3 |

Erythema and edema are recorded according to the same grading scale.

2.5—Interpretation of the results

The scores obtained for erythema and edema are added.

All the animals which show a score equal to or greater than 2 after the challenge phase are regarded as being positive.

All the other signs (such as stingings, blisters, and the like) are also taken into consideration in the interpretation.

The sensitizing ability is defined by the percentage of positive animals according to the following scale:

| Percentage | Class | Classification |
| --- | --- | --- |
| 0–8 | I | Very light |
| 9–28 | II | Light |
| 29–64 | III | Moderate |
| 65–80 | IV | Strong |
| 81–100 | V | Very strong |

RESULTS

1—Concentrations to be used

For the induction: 1/1

For the challenge phase: 1/1 (MNIC) and 1/2 (1/2 MNIC)

2—Determination of a sensitizing ability

All microscopic reaction was recorded, both in the control group and in the treated group, whatever the concentration used.

CONCLUSION

Under the experimental conditions employed, the product of the invention, lipophilized malic acid according to the invention used at 20% in distilled water, did not induce a macroscopic reaction which could be related to a sensitization in albino guinea pigs.

The product can consequently be regarded as being hypoallergenic.

Example 19 of the Invention

In Vivo Tests of Keratolytic Activity on Adult Caucasian Volunteers

A—Method

In order to determine the keratolytic activity of the lipophilized hydroxylated acids according to the invention, cosmetic formulations containing increasing amounts of lipophilized hydroxylated acids according to the invention were prepared and then tested on panels of 10 volunteers of adult Caucasian type. Each panel compared a keratolytic formula to the corresponding placebo formula. An untreated site was retained for comparison. The test was carried out on circular regions with a diameter of 25 mm, delimited on the inner face of the forearms using self-adhesive rings. These regions had been impregnated beforehand on three occasions and at intervals of 6 h with a cosmetic formulation containing 10% dihydroxyacetone.

The creams tested were delivered in a fixed amount of 1 ml on day 1, 3, 5, 7, 10 and 12. The regions concerned are covered for ½ hour with an absorbent aerated compress which absorbs the excess product. The differences in coloring are noted visually before each application.

B—Compositions tested

The compositions tested during this study are the following:

1—a placebo composition, prepared at a pH of 5.5, which does not contain keratolytic agent and which has the following percentage formulation:

| Phase A |  |  |
| --- | --- | --- |
| Sodium dihydroxycetyl phosphate (and) isopropyl hydroxycetyl ether |  | 2% |
| Glycerol |  | 3% |
| Propylene glycol |  | 2% |
| Water | q.s. for | 100% |
| Phase B |  |  |
| Glycol stearate |  | 14% |
| Triisononanoin |  | 5% |
| Octyl cocoate |  | 6% |
| Phase C |  |  |
| Bactericidal agent based on butylene glycol and parabens commercially available under the name Bactericide MB, company DRAGOCO |  | 1% |
| Phenoxyethanol and parabens |  | 1% |

This placebo composition is prepared conventionally by emulsifying Phase B in Phase A with stirring and by then adding the bactericidal agent of Phase C.

2—Composition $A_1$, prepared at a pH of 5.5, containing 4% malic acid

The preparation of this composition $A_1$ is as described for the manufacture of the placebo composition but Phase A contains 4% of malic acid.

3—Compositions of the invention $I_1$, $I_2$, $I_3$

These compositions $I_1$, $I_2$, $I_3$ are prepared as described for the placebo composition, except that Phase A contains increasing amounts of the compound according to the invention of Example 1 comprising a stearic acid/malic acid anhydride and ester bond mixture, the equivalent concentration of the malic acid part in the compound of the invention representing respectively 2%, 4% and 6% of the compositions $I_1$, $I_2$, $I_3$. The two compositions are also prepared at pH 5.5.

In order to adjust the pH to 5.5 for each of these placebo, $A_1$ and $I_1$, $I_2$, and $I_3$ compositions, the pH is adjusted using concentrated hydrochloric acid or concentrated sodium hydroxide solution.

C—Results

Repeated applications of a formulation based on dihydroxyacetone (DHA) makes it possible to color the upper layers of the skin as would a "self-tanning" product. The decoloring of a region thus treated requires 15 days. The application to such a region of a cosmetic formulation containing a keratolytic active agent will make it possible to obtain a faster decoloring. Measuring this decoloring every three days for 15 days makes it possible to study the keratolytic power of the active principles studied.

Such a decoloring is measured with a Minolta chromameter. The light parameters L, a and b are calculated in the form of a mean of 5 experimental data for each subject and for each period monitored.

The mean color difference $\Delta E^*ab = (\Delta L^2 + \Delta a^2 + \Delta b^2)^{1/2}$ is calculated between each site treated and the control region (colored with DHA but not treated with one of the compositions).

If $T_0$ is the beginning of the experiment and $T_F$ the finish of the experiment (see FIG. 1), $\Delta E$ represents the variation in color intensity between the control region defined by Curve I, in this case consisting of a straight line, extending from the color intensity point $C_0$ at $T_0$ to the color intensity point $C_F$ at $T_F$, and a zone treated with a keratolytic composition defined by Line II, FIG. 1, in this case also consisting of a straight line extending from the color intensity point $C_0$ to the color intensity point $C_F$, which is in this case obtained at time $T_{\Delta Emax}$. This variation should increase to a maximum ($\Delta E_{max}$) achieved for $T_{\Delta Emax}$, and should then decrease.

Such variations depend on the keratolytic property of each composition. The surface between the two curves is directly proportional to the keratolytic power intensity of each composition.

Thus, applications of the compositions indicated above, respectively the placebo composition, the comparison composition $A_1$ and the compositions of the invention I1, $I_2$, $I_3$, according to the method described above, make it possible to observe the following results:

a) The placebo composition causes the disappearance of part of the coloring, which is notable from the 8th day. This observation is confirmed throughout the 15 days of the experiment required for obtaining complete decoloring. This means that this preparation has a weak but real keratolytic power. This power may arise from the massaging during the application of the cream as well as from the moisturing power of the cream which, by detaching the corneocytes, thus makes possible a slightly faster than normal desquamation.

b) The four keratolytic compositions, $A_1$, $I_1$, $I_2$, and $I_3$ respectively, are very strongly keratolytic. In fact, 7 days after the beginning of the tests, the decoloring is already virtually complete, which means that the time required for causing desquamation of the colored layers is halved, from 15 days to 7 days. This result is confirmed by the measurement with a chromameter with respect to time.

The measurements with the chromameter obtained with respect to time for each of the compositions tested, $A_1$, $I_1$, $I_2$ and $I_3$, are recorded in Table I below, expressed as mean color intensity difference $\Delta E$ in accordance with the standard of FIG. 1.

TABLE I

| Emulsion containing | Time | D3 | D5 | D7 | D10 | D12 | D15 | Sum D3 to D15 |
|---|---|---|---|---|---|---|---|---|
| Nothing (placebo) | Mean | 0.87 | 1.20 | 0.95 | 1.24 | 0.34 | 0.03 | 4.64 |
| | SD* | 0.39 | 0.45 | 0.25 | 0.41 | 0.58 | 0.22 | 2.29 |
| Lipophilized malic acid, corresponding to a 2% concentration of free malic acid ($I_1$) | Mean | 2.94 | 3.90 | 3.87 | 3.20 | 1.43 | 0.36 | 15.70 |
| | SD* | 0.99 | 1.13 | 0.66 | 0.77 | 0.61 | 0.44 | 4.80 |
| Lipophilized malic acid, corresponding to a 4% concentration of free malic acid ($I_2$) | Mean | 4.93 | 6.99 | 8.26 | 7.64 | 4.76 | 0.94 | 33.52 |
| | SD* | 0.84 | 0.97 | 1.16 | 1.50 | 1.75 | 0.75 | 6.97 |
| Lipophilized malic acid, corresponding to a 6% concentration of free malic acid ($I_3$) | Mean | 4.70 | 6.80 | 7.71 | 7.04 | 4.87 | 1.29 | 32.40 |
| | SD* | 1.05 | 1.14 | 0.68 | 1.12 | 4.54 | 1.28 | 6.81 |
| Free malic acid at a concentration of 4% in the formulation ($A_1$) | Mean | 4.58 | 6.73 | 7.63 | 6.93 | 4.98 | 1.80 | 32.64 |
| | SD* | 1.05 | 1.21 | 1.05 | 1.12 | 1.44 | 1.29 | 7.17 |

SD* = Standard Deviation

Figure 2:
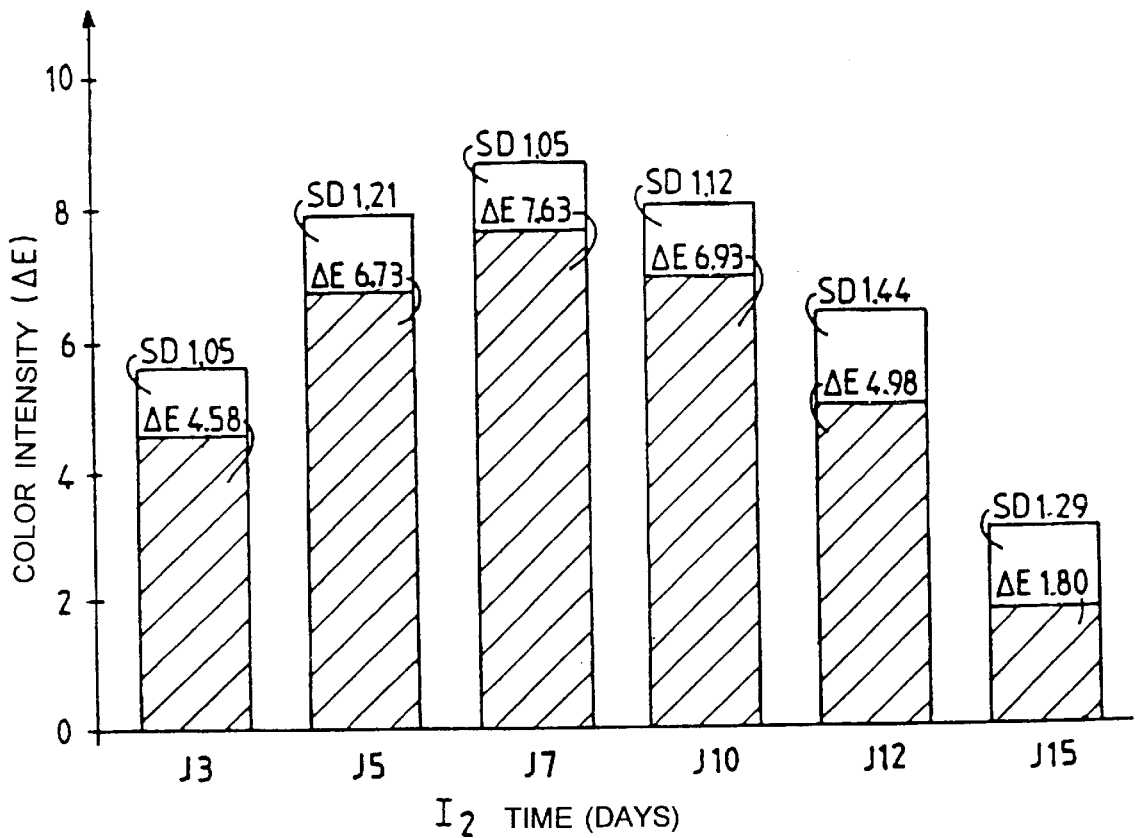
FIG. 2 represents a bar chart example obtained with a keratolytic composition comprising a lipophilic compound of Example 1 of the invention (I2) based on a stearic acid/malic acid anhydride and ester mixture, corresponding to 4% of free malic acid, as a function of the time, expressed in days, on the abscissa and also as a function of the color intensity, expressed as color difference $\Delta E$, on the ordinate, in accordance with FIG. 1.

By way of example, the color intensity differences obtained with the composition of the invention $I_2$, are recorded in bar chart form in FIG. 2, the color intensity differences $\Delta E$ being represented in black and the standard deviation SD being added in the form of a gray bar.

Figure 3:
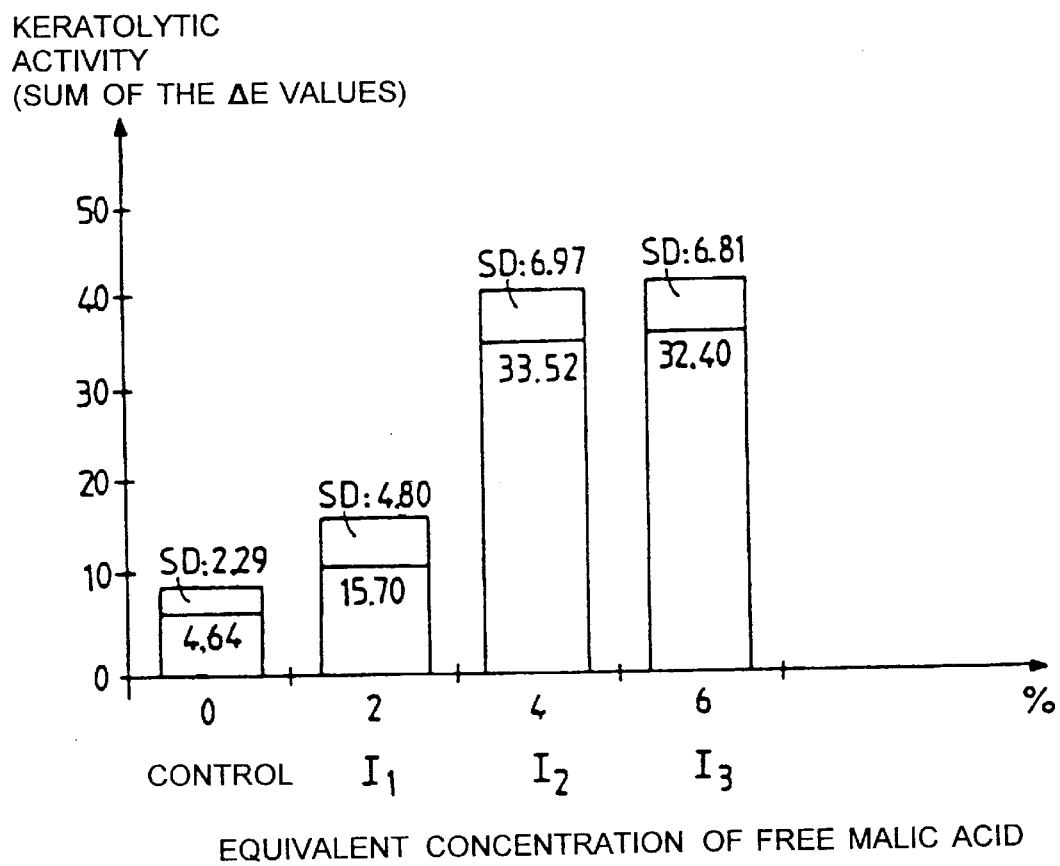
FIG. 3 represents the test results obtained with various compounds of the invention $I_1$, $I_2$, and $I_3$, as detailed in Example 19, as a function of the acid concentration expressed as equivalent free acid and the keratolytic activity, on the ordinate, expressed in the form of area or surface resulting from the sum of all the color differences $\Delta E$ between Curves I and II plotted in FIG. 1 and as explained in relation to FIG. 1.

In addition, the sum of all the color intensity differences $\Delta E$ obtained with the placebo composition and the compositions of the invention, $I_1$, $I_2$, and $I_3$, are recorded in FIG. 3 with respect to the equivalent concentration of free malic acid, in black, the standard deviation SD being added in gray.

It should be noted that the test results obtained with 4% free malic acid in positive control form mentioned in Table I are not shown in FIG. 3 since the bars obtained are essentially identical to those of the composition of the invention $I_2$, and cannot be differentiated from the latter.

From these test results, it may be observed that, for the same equivalent concentration of malic acid, the composition containing lipophilized malic acid ($I_2$) has a keratolytic power or intensity which is as strong as the composition containing free malic acid ($A_1$).

The lipophilized malic acid according to the invention and described in Example 1 of the present invention has a keratolytic power or intensity as strong as free malic acid.

c) Among the two keratolytic compositions, Al and $I_2$ respectively, composition $I_2$, prepared with lipophilized lactic acid according to the present invention, was perfectly well tolerated by the various volunteers and caused no stinging, no irritation and no inflammation whereas stinging and blotches were perceptible in the case of the free malic acid used in the formulation of the composition $A_1$.

d) Among all the keratolytic compositions containing lipophilized malic acid, that is to say $I_1$ (4.3% of lipophilized malic acid, corresponding to an equivalent concentration of malic acid of 2%), $I_2$ (8.7% of lipophilized malic acid, corresponding to an equivalent concentration of malic acid of 4%) and $I_3$ (13% of lipophilized malic acid, corresponding to an equivalent concentration of malic acid of 6%), $I_2$, and $I_3$ are the most powerful keratolytic compositions (see FIG. 3).

On increasing the concentration of lipophilized malic acid in the compositions, an increase in the keratolytic properties of such compositions is obtained.

Such an increase is stabilized at a plateau for high concentrations, very probably due to a maximum storage capacity of the skin.

A description is now given below of various cosmetic or pharmaceutical and/or dermatological composition formulation examples.

Example 20 of the Invention

Cosmetic Composition Possessing a Keratolytic Effect

This composition has the following percentage composition:

| | | |
|---|---|---|
| Malic acid/stearic acid lipophilic hydroxylated acid of Example 1 | 10% | |
| Salicylic acid | 0.5% | |
| Urea | 4% | |
| Cosmetic excipient | q.s. for | 100% |

Example 21 of the Invention

Cosmetic Composition Possessing an Anti-acne Effect

This composition has the following percentage composition:

| | | |
|---|---|---|
| Salicylic acid/undecylenic acid lipophilic hydroxylated acid of Example 4 | 4% | |
| Pharmaceutical excipient | q.s. for | 100% |

Example 22 of the Invention

Cosmetic Composition Possessing an Anti-dandruff Activity

This composition has the following ingredients in percentage by weight:

| | | |
|---|---|---|
| Lipophilic hydroxylated acid of Example 16 (malic acid/laurylamine) | 10% | |
| Pharmaceutical excipient | q.s. for | 100% |

Example 23 of the Invention

Moisturizing Pharmaceutical Composition

| | | |
|---|---|---|
| Lipophilic hydroxylated acid of Example 6 (serine/linolenic and stearic acid) | 5% | |
| Urea | 2% | |
| Cosmetic excipient | q.s. for | 100% |

Example 24 of the Invention

Pharmaceutical Composition for Treating Ichthyotic Skins, Psoriasis or Eczemas

| | | |
|---|---|---|
| Lipophilic hydroxylated acid of Example 4 (salicylic acid/undecylenic acid) | 6% | |
| Lipophilic hydroxylated acid of Example 2 (glycolic acid/palmitic acid) | 6% | |
| Pharmaceutical excipient | q.s. for | 100% |

Example 25 of the Invention

Restructuring Anti-age Formulation

| Phases | | Amounts (%) |
|---|---|---|
| A/ | Ether of polyethylene glycol (2) and of stearyl alcohol | 3 |
| | Ether of polyethylene glycol (21) and of stearyl alcohol | 2 |
| | Isostearyl isostearate | 4 |
| | Apricot kernel oil | 4 |
| | Safflower oil | 2 |
| | Dimethicone 556 | 2 |
| | Cetostearyl alcohol | 3 |
| B/ | Glycerol | 5 |
| | Lipophilic hydroxylated acid of Example 1 (malic acid/stearic acid) | 6 |
| | Water                    q.s. for | 100 |
| C/ | Phenoxyethanol and mixture of parabens | 0.5 |
| | Propylene glycol | 0.5 |
| D/ | Phenoxyethanol | 0.3 |
| | α-Tocopherol | 0.05 |

Phases A and B are heated separately to 75° C. with moderate stirring. The pH of Phase B is adjusted to the desired pH value. A is poured into B with very vigorous stirring (of the Silverson or Ultraturrax type) and then the temperature is allowed to fall with slow stirring. The components of Phases C and D are added at 30° C.

Example 26 of the Invention

Anti-wrinkle Formulation

| Phases | | Amounts (%) |
|---|---|---|
| A/ | Isostearyl isostearate | 4 |
| | Safflower oil | 4 |
| | Oleyl erucate | 2 |
| | Dimethicone | 5 |
| | Cetostearyl alcohol | 3 |
| | Lipophilic hydroxylated acid of Example 1 (malic acid/stearic acid) | 3 |

-continued

| Phases | | Amounts (%) |
|---|---|---|
| B/ | Glycerol | 5 |
| | Water q.s. for | 100 |
| C/ | Phenoxyethanol and mixture of parabens | 0.5 |
| | Propylene glycol | 0.5 |
| D/ | Phenoxyethanol | 0.3 |

Phases A and B are heated separately to 75° C. with moderate stirring. The pH of the formula is conditioned in this case by the pH of the lipophilic hydroxylated acid. A is poured into B with very vigorous stirring (of the Silverson or Ultraturrax type) and the temperature is then allowed to fall with slow stirring. The components of Phases C and D are added at 30° C. If necessary, the preparation is adjusted to the desired pH using, for example, lactic acid.

It should be noted that the product of the invention is also used as emulsifying agent in this formulation.

Example 27 of the Invention

Face, Dry Skins Formulation

| Phases | | Amounts (%) |
|---|---|---|
| A/ | Borage oil | 2 |
| | Safflower oil | 4 |
| | Caprylic/capric triglyceride | 6 |
| | Cetostearyl alcohol | 3 |
| B/ | Glycerol | 5 |
| | Water q.s. for | 100 |
| | Lipophilic hydroxylated acid of Example 2 (glycolic acid/palmitic acid) | 4 |
| C/ | Phenoxyethanol and mixture of parabens | 0.5 |
| | Propylene glycol | 0.5 |
| D/ | Phenoxyethanol | 0.3 |

Phases A and B are heated separately to 75° C. with moderate stirring. The pH of Phase B is adjusted to the desired pH of the formulation. A is poured into B with very vigorous stirring (of the Silverson or Ultraturrax type) and the temperature is then allowed to fall with slow stirring. The components of Phases C and D are added at 30° C. If necessary, the preparation is adjusted to the desired pH using, for example, lactic acid.

It should be noted that the product of the invention is also used as emulsifying agent in the formulation (absence of other emulsifying agents in the formula).

What we claim is:

1. A method of treatment of skin for keratolytic activity comprising applying to said skin a lipophilic hydroxylated acid compound which is the reaction product of a hydroxylated acid selected from the group consisting of glycolic acid, lactic acid, malic acid, tartaric acid, gluconic acid, citric acid, salicylic acid, serine, a glycolic acid polymer, a lactic acid polymer, a glycolic acid and a lactic acid copolymer, with at least one hydrophobic hydrocarbon component, selected from the group consisting of a halide or anhydride of stearic acid, a halide or anhydride of palmitic acid, a halide or anhydride of myristic acid, a halide or anhydride of lauric acid, a halide or anhydride or undecylenic acid, a halide or anhydride of oleic acid, a halide or anhydride of linoleic acid, and a halide or anhydride of linolenic acid, in an amount effective to perform said treatment of skin.

2. The method of claim 1, wherein the compound is in a final reaction mixture of the lipophilic hydroxylated acid compound with the unreacted hydroxylated acid and the unreacted hydrophobic hydrocarbon component.

3. The method of claim 1, wherein the compound is in a lyophilized form of a final reaction mixture of the lipophilic hydroxylated acid compound with the unreacted hydroxylated acid and the unreacted hydrophobia hydrocarbon component in the reaction medium.

4. The method of claim 1, wherein said lipophilic hydroxylated acid compound is present in a cosmetic or pharmaceutical composition at a concentration ranging between 0.1 weight % and 50 weight % with respect to the total weight of the final composition.

5. The method of claim 1, wherein said lipophilic hydroxylated acid compound is present in a cosmetic or pharmaceutical composition at a concentration ranging between 1 weight % and 10 weight % with respect to the total weight of the final composition.

6. The method of claim 1, wherein said treatment of skin for keratolytic activity is a treatment for performing an anti-aging effect on the skin.

7. The method of claim 1, wherein said treatment of skin for keratolytic activity is a treatment selected from the group consisting of a treatment for stimulating the skin cells, a treatment for improving the elasticity and the cohesion of the skin, a method for depigmenting the skin and a method for performing an anti-wrinkle effect of the skin.

* * * * *